US007803587B2

(12) United States Patent
Lee et al.

(10) Patent No.: US 7,803,587 B2
(45) Date of Patent: Sep. 28, 2010

(54) **METHOD FOR DEVELOPING CULTURE MEDIUM USING GENOME INFORMATION AND *IN SILICO* ANALYSIS**

(75) Inventors: Sang Yup Lee, Daejeon (KR); Ho Nam Chang, Daejeon (KR); Hyohak Song, Daejeon (KR); Tae Yong Kim, Yongin-si (KR); Bo-Kyung Choi, Gyeongsangnam-do (KR)

(73) Assignee: Korea Advanced Institute of Science and Technology, Daejon (KR)

( * ) Notice: Subject to any disclaimer, the term of this patent is extended or adjusted under 35 U.S.C. 154(b) by 670 days.

(21) Appl. No.: 11/743,668

(22) Filed: May 2, 2007

(65) Prior Publication Data

US 2008/0003661 A1   Jan. 3, 2008

(30) Foreign Application Priority Data

May 4, 2006   (KR)   ........................ 10-2006-0040581

(51) Int. Cl.
*C12P 7/44*   (2006.01)
*C12N 1/20*   (2006.01)
*C12Q 1/00*   (2006.01)
*C12Q 1/68*   (2006.01)
*G06G 7/48*   (2006.01)

(52) U.S. Cl. ............................... 435/142; 435/4; 435/6; 435/11; 435/253.6; 703/11

(58) Field of Classification Search ........................ None
See application file for complete search history.

(56) References Cited

U.S. PATENT DOCUMENTS

| 5,143,834 | A |   | 9/1992 | Glassner et al. |
| 5,168,055 | A |   | 12/1992 | Datta et al. |
| 5,504,004 | A |   | 4/1996 | Guettler et al. |
| 5,521,075 | A |   | 5/1996 | Guettler et al. |
| 5,573,931 | A |   | 11/1996 | Guettler et al. |
| 5,604,177 | A | * | 2/1997 | Kinnersley et al. .......... 504/147 |
| 5,770,435 | A |   | 6/1998 | Donnelly et al. |
| 7,241,594 | B2 | * | 7/2007 | Lee et al. .................... 435/71.2 |
| 7,351,578 | B2 | * | 4/2008 | Cheo et al. ................. 435/320.1 |
| 7,393,632 | B2 | * | 7/2008 | Cheo et al. ...................... 435/6 |

FOREIGN PATENT DOCUMENTS

WO   2005052135 A1   6/2005

OTHER PUBLICATIONS

Cowan, Don, "Genomics: Use your neighbour's genes", "Nature", Sep. 28, 2000, pp. 466-467, vol. 407, No. 6803.
Dasu, Venkata, et al., "Development of Medium for Griseofulvin Production—Part 1 . Screening of Medium Constituents Using the Plackett—Burma", "J. Microbiol. Biotechnol.", Jun. 28, 2002, pp. 355-359, vol. 12, No. 3.
Dasu, Venkata, et al., "Development of Medium for Griseofulvin Production—Part 2 . Optimization of Medium Conatituents Using Central Composite", "J. Microbiol. Biotechnol.", Jun. 28, 2002, pp. 360-366, vol. 12, No. 3.
Grobben, G.J., et al., "Enhancement of Exopolysaccharide Production by *Lactobacillus delbrueckii* subsp. bulgaricus NCFB 2772 with a . . . ", "Appl. Environ. Microbiol.", Apr. 1998, pp. 1333-1337, vol. 64, No. 4.
Hong, Soon Ho, et al, "The genome sequence of the capnophilic rumen bacterium *Mannheimia succiniciproducens*", "Nature Biotechnol.", Oct. 2004, pp. 1275-1281, vol. 22, No. 10.
McKinlay, James B., et al., "Insights into *Actinobacillus succinogenes* Fermentative Metabolism in a Chemically Defined Growth Medium ", "Appl. Environ. Microbiol.", Nov. 2005, pp. 6651-6656, vol. 71, No. 11.
NG, Wailap Victor, et al., "Genome sequence of *Halobacterium* species NRC-1 ", "Proc. Natl. Acad. Sci. USA", Oct. 24, 2000', pp. 12176-12181, vol. 97, No. 22.
NG, Wailap Victor, et al., "Fig 2. Genetic map of the *Halobacterium* NRC-1 chromosome (2,014,239 bp) and two minichromosomes, pNRC200 (365,425 bp) . . . ", "Proc. Natl. Acad. Sci. USA", Oct. 24, 2000, vol. 97, No. 22.
NG, Wailop Victor, et al., "Table 2. *Halobacterium* NRC-1 genes and genetic elements", "Proc. Natl. Acad. Sci. USA", Oct. 24, 2000, vol. 97, No. 22.
Nierman, William C. et al., "Complete genome sequence of Caulobacter crescentus ", "Proc. Natl. Acad. Sci. USA", Mar. 20, 2001, pp. 4136-4141, vol. 98, No. 7.
Nierman, William C., et al., "Fig. 4. Linear representation of the *Caulobacter crescentus* genome", "Proc. Natl. Acad. Sci. USA", Mar. 20, 2001, vol. 98, No. 7.
Perna, Nicole T., et al., "Genome sequence of enterohaemorrhagic *Escherichia coli* O157:H7 ", "Nature", Jan. 25, 2001, pp. 529-533, vol. 409, No. 6819.
Rizzino, Angie, et al., "Growth of Embryonal Carcinoma Cells in Serum-Free Medium ", "Proc. Natl. Acad. Sci. USA", Apr. 1, 1978, pp. 1844-1848, vol. 75, No. 4.
Ruepp, Andreas, et al., "The genome sequence of the thermoacidophilic scavenger *Thermoplasma acidophilum*", "Nature", Sep. 28, 2000, pp. 508-513, vol. 407, No. 6803.
Samuelov, N.S., et al., "Influence of CO2-HCO3 Levels and pH on Growth, Succinate Production, and Enzyme Activities of *Anaerobiospirillum* . . . ", "Appl. Environ. Microbiol.", Oct. 1991, pp. 3013-3019, vol. 57, No. 10.

(Continued)

*Primary Examiner*—Herbert J. Lilling
(74) *Attorney, Agent, or Firm*—Steven J. Hultquist; Intellectual Property / Technology Law; Kelly K. Reynolds

(57) ABSTRACT

A method for developing a culture medium using genome information and in silico analysis. In one implementation, the method involves developing a minimal synthetic medium, including the steps of constructing a metabolic network using genome information of prokaryotic cell or eukaryotic cell, selecting components of the minimal synthetic medium removing any one among external metabolites from the constructed metabolic network and conducting metabolic flux analysis using in silico simulation, and determining a final culture medium by actual culture.

17 Claims, 5 Drawing Sheets

OTHER PUBLICATIONS

Teusink, Bas, et al., "In Silico Reconstruction of the Metabolic Pathways of *Lactobacillus plantarum*: Comparing Predictions of Nutrient . . . ", "Appl. Environ. Microbiol.", Nov. 2005, pp. 7253-7262, vol. 71, No. 11.

Willke, TH., et al., "Industrial bioconversion of renewable resources as an alternative to conventional chemistry ", "Appl. Microbiol. Biotechnol.", Dec. 2004, pp. 131-142, vol. 66, No. 2.

Zeikus, J.G., et al., "Biotechnology of succinic acid production and markets for derived industrial products ", "Appl. Microbiol. Biotechnol.", May 1999, pp. 545-552, vol. 51, No. 5.

Adams, Mark D., et al., "The Genome Sequence of *Drosophila melanogaster*", "Science", Mar. 24, 2000, pp. 2185-2195, vol. 287, No. 5461.

Ajinomoto Group, "Environmental Report 2003", 2003, p. 21.

Cocaign-Bousquet, M., et al., "Rational development of a simple synthetic medium for the sustained growth of *Lactococcus lactis*", "J. Appl. Bacteriol.", 1995, pp. 108-116, vol. 79.

Davis, C.P., et al., "*Anaerobiospirillum*, a new genus of spiral-shaped bacteria", "Int. J. Sys. Bacteriol.", Oct. 1976, pp. 498-504, vol. 26, No. 4.

Hong, Soon Ho, et al., "Metabolic flux analysis for succinic acid production by recombinant *Escherichia coli* with amplified malic enzyme . . . ", "Biotechnol. Bioeng.", Jul. 20, 2001, pp. 89-95, vol. 74, No. 2.

Lee, Pyung Cheon, et al., "Succinic acid production by *Anaerobiospirillum succiniciproducens*: effects of the H2/CO2 supply and glucose . . . ", "Enzyme Microbial Technol.", Jun. 1, 1999, pp. 549-554, vol. 24, No. 8-9.

Lee, Pyung Cheon, et al., "Succinic acid production with reduced by-product formation in the fermentation of *Anaerobiospirillum succiniciproducens* ", "Biotechnol. Bioeng.", Jan. 5, 2001, pp. 41-48, vol. 72, No. 1.

Lee, P., et al., "Isolation and characterization of a new succinic acid-producing bacterium, *Mannheimia succiniciproducens* MBEL55E, . . . ", "Appl. Microbiol. Biotechnol.", Apr. 2002, pp. 663-668, vol. 58, No. 5.

Lin, Henry, et al., "Fed-batch culture of a metabolically engineered *Escherichia coli* strain designed for high-level succinate production . . . ", "Biotechnol. Bioeng.", Jun. 20, 2005, pp. 775-779, vol. 90, No. 6.

Lin, H., et al., "Metabolic engineering of aerobic succinate production systems in *Escherichia coli* to improve process productivity . . . ", "Metab. Eng.", Mar. 2005, pp. 116-127, vol. 7, No. 2.

Mantha, D., et al., "Optimization of medium composition by response surface methodology for the production of tartaric acid by . . . ", "Bioprocess Eng.", Oct. 1998, pp. 285-288, vol. 19, No. 3.

Urbance, Susan E., et al., "Evaluation of succinic acid continuous and repeat-batch biofilm fermentation by *Actinobacillus succinogenes* using . . . ", "Appl.. Microbiol. Biotechnol.", Nov. 2004, pp. 664-670, vol. 65, No. 6.

Vemuri, G.N., et al, "Succinate production in dual-phase *Escherichia coli* fermentations depends on the time of transition from aerobic to . . . ", "J. Ind. Microbiol. Biotechnol.", Jun. 2002, pp. 325-332, vol. 28, No. 6.

Zhang, J., et al., "Chemically defined media for commercial fermentations ", "Appl. Microbiol. Biotechnol.", Apr. 1999, pp. 407-421, vol. 51, No. 4.

* cited by examiner (A)

(B)

(A)

(B)

(C)

(D)

METHOD FOR DEVELOPING CULTURE MEDIUM USING GENOME INFORMATION AND IN SILICO ANALYSIS

CROSS REFERENCE TO RELATED APPLICATION

This application claims priority under 35 USC 119 of Korean Patent Application No. 10-2006-0040581 filed May 4, 2006. The disclosure of Korean Patent Application No. 10-2006-0040581 is hereby incorporated herein in its entirety, for all purposes.

BACKGROUND OF THE INVENTION

1. Field of the Invention

The present invention relates to a method for developing a culture medium using genome information and in silico analysis. More particularly, it relates to a method for developing a minimal synthetic medium, the method comprising constructing a metabolic network using genome information of prokaryotic cell or eukaryotic cell, selecting components of the minimal synthetic medium removing any one among external metabolites from the constructed metabolic network and conducting metabolic flux analysis using in silico simulation, and determining a final culture medium by actual culture.

2. Background of the Related Art

The culture of prokaryotic cells or eukaryotic cells in a specific environment requires various nutrients. The specific nutrient requirements vary according to the kind of animals, plants, insects and microorganisms, or the kind of cell tissues or organs to be cultured and thus the medium composition for each culture is different. The culture of eukaryotic cell or prokaryotic cell requires combination medium containing a proper combination of nutrients, hormone, growth factor and blood serum, in general, a medium prepared by adding inorganic salts, amino acids and vitamins to the medium containing the extract of cells or cell lines to be cultured.

In a case of blood serum, although Sato et al established non-blood serum culture method by adding known components to a medium without adding blood serum (Rizzino et al., PNAS, 75:1844, 1978), the final culture medium contains a tissue extract in which various unknown chemicals exist. Some of unknown compounds came from a tissue extract could inhibit the growth of cells and cell lines. Especially, they can cause a fatal risk in patients when cells or cell lines are cultured and used for treatment. For biopharmaceuticals production, they not only decrease the productivity but also increase the costs of separation and purification. Therefore, the development of a culture medium in which all components are known and well clarified is required in order to insure safety in use and elucidate the roles of individual components of culture media for the production of biopharmaceutical products or the treatment through the culture of cell lines or cells of insects, plants and animals.

Complex or semi-defined media which contain peptone, yeast extract, corn steep liquor, blood serum, beef stock, and/or malt extracts, etc, they are composed of numerous unknown compounds, are normally used for the culture of microorganisms. However, their qualities and compositions vary with manufacture dates, manufacturing enterprises, and manufacturing materials. In addition, the prices of them are more expensive than those of chemicals used in preparation of chemically defined, synthetic media. Also, use of a complex medium containing the aforementioned materials cannot guarantee the production of goods with consistent quality through microorganisms cultivation and unknown components in the complex medium cause an increase in the costs of separation and purification. It has been reported that some unknown components present in complex and semi-defined media inhibit cell growth and production of specific metabolites (Zhang et al., Appl. Microbiol. Biotechnol., 51:407, 1997). Moreover, unknown components in the complex medium make it difficult to understand exact cellular metabolic characteristics and thus restrict the development of excellent bacteria using metabolic engineering technique.

Therefore, numerous researches have focused on the development of chemically defined media to overcome shortcomings in using complex media which include the aforementioned materials. In fact, synthetic media have been developed and employed for the production of exopolysaccharides and lactic acid through microbial fermentation (Cocaign-Bousquet et al., J. Appl. Bacteriol., 79:108, 1995; Grobben et al., Appl. Environ. Microbiol., 64:1333, 2003).

To date, a synthetic medium have been developed by using a single omission technique, in which a single component is sequentially eliminated from a culture medium containing all nutrient components. After observing whether cells can grow in a medium in the absence of a single component, components essential for cell growth are identified and a synthetic medium are formulated. (Zhang et al., Appl. Microbiol. Biotechnol., 51:407, 1997). However, a single omission technique is based on a trial and error method, indicating that this method is laborious, time-consuming, and costly. In order to overcome the above shortcomings, although various statistical methods have been developed and employed for identifying components necessary for cell growth and thus formulating a synthetic medium, these methods are also based on a trial and error method and their success is very low.

Various techniques based on statistical method such as Plackett-Burman experimental design, fractional factorial experimental design, central composite experimental design, and response surface technique have been applied to develop a synthetic medium (Dasu et al., J. Microbiol. Biotechnol., 12:355, 2002; Dasu et al., J. Microbiol. Biotechnol., 12:360, 2002; Mantha et al., Bioprocess Eng., 19:285, 1998).

Since human genome map was completed in the 2003 after the completion of human genome project, till now, the whole genome sequences of more than 300 species of organisms has been deciphered. Also, now, many researchers are making a major contribution to reveal genome sequences of various organisms and constructing a metabolic network based on the revealed genome information (Ng et al., PNAS, 97:12176, 2000; Ruepp et al., Nature, 407:466, 2000; Nierman et al., PNAS, 98:4136, 2001; Perna et al., Nature, 409:529, 2001; Adams et al., Science, 287:2185, 2000).

Succinic acid ($HOOCCH_2CH_2COOH$) is a high functional basic chemical having various industrial applications ranging from a precursor of chemicals to foods and pharmaceuticals (Zeikus et al., Appl. Microbiol. Biotechnol., 51:545, 1999). Since the usage of succinic acid as a raw material of polybutylene succinate (Ajinomoto, Environ. Rep., 21, 2003) and polyamides, which are major biodegradable polymers (Willke et al., Appl. Microbiol. Biotechnol., 66:131, 2004), is verified recently, its dramatic demand thereof is expected.

Succinic acid can be produced by chemical synthesis and conventional microbial fermentation. Only a small amount of succinic acid is produced through microbial fermentation for specific uses such as foods and pharmaceuticals. On the other hand, most commercial succinic acid is synthesized using liquid propane gas LPG or n-butane from crude oil, and this chemical process yield large amounts of harmful wastes, waste water, and waste gas. Particularly, it has a limitation in that it uses fossil fuel as a starting material, and recent increase of crude oil price causes an increase in the price of succinic acid.

In addition, with an increased interest in eco-friendly processes, many researchers have made extensive efforts to develop economical and eco-friendly succinic acid production process in order to solve the problems caused by the chemical synthetic processes. Recently, the production of succinic acid through microbial fermentation using renewable resources has drawn a significant attention as an alternative succinic acid production process.

Researches on succinic acid production through microbial fermentation can be divided into fermentation process development, the development of separation and purification processes, and the development of cheaper substrates and excellent bacteria. The representative succinic acid-producing bacteria are recombinant *E. coli, Anaerobiospirillum* and ruminal bacteria *Actinobacillus,: Bacteroides, Mannheimia, Succinimonas* and *Succinivibrio* etc.

Chicago University research group in the United States created recombinant *E. coli* NZN111 strain, in which ldh and pfl genes participating in the production of lactic and formic acids, respectively, were deleted to enhance succinic acid production. This research group further created an AFP111 (ATCC 202021) strain by manipulating a glucose transport gene ptsG in the NZN111 strain (U.S. Pat. No. 5,770,435). Also, the present inventors overexpressed a malic gene (sfcA) involved in the production of succinic acid in the NZN111 strain, which successfully increased succinic acid production as well as effectively prevented pyruvic acid accumulation (Hong et al., *Biotechnol. Bioeng.*, 74:89, 2001). Also, Georgia University research team in the United States made an attempt to increase succinic acid production by an AFP111/pTrc99A-pyc strain obtained by overexpressing pyruvate carboxylase gene(pyc) of *Rhizobium etli* strain in the AFP111 strain (Vemuri et al., *J. Ind. Microbiol. Biotechnol.*, 28:325, 2001). More recently, Rice University research team in the United States created various recombinant *E. coli* strains by manipulating genes involved in glycolysis, tricarboxylic acid (TCA) cycle, and glyoxylate pathways, which induced succinic acid production under an aerobic condition (Lin et al., *Metabol. Eng.*, 7:116, 2005; Lin et al., *Biotechnol. Bioeng.*, 90:775, 2005).

*Anaerobiospirillum succiniciproducens* strain identified in gullet and excrement from German hunting dogs has an ability to produce a large amount of succinic acid under absolute anaerobic conditions (Davis et al., *Int. J. Syst. Bacteriol.*, 26:498, 1976; Samuelov et al., *Appl. Environ. Microbiol.*, 57:3013, 1991). Accordingly, the present inventors have conducted studies with respect to various kinds of carbon sources, nitiride nitrogen sources, and gas components ($CO_2$/$H_2$) for the production of succinic acid using *Anaerobiospirillum succiniciproducens*. (Lee et al., *Enzyme Microbial Technol.*, 24:549, 1999; Lee et al., *Biotechnol. Bioeng.*, 72:41, 2001). Also, Michigan Biotechnology Institute(MBI) International research group developed a process for the production of succinic acid and purification thereof using the above bacteria (U.S. Pat. No. 5,521,075; U.S. Pat. No. 5,168,055; U.S. Pat. No. 5,143,834).

Among rumen bacteria, *Actinobacillus* and *Menheimia* are relatively widely studied. MBI research group created an *Actinobacillus succinogenes* 130Z strain (ATCC 55618) and other mutants resistant to sodium monofluoroacetate and used them in the succinic acid production process with high concentration (U.S. Pat. No. 5,504,004; U.S. Pat. No. 5,573,931). Recently, there has been an attempt to increase the production of succinic acid through a repeated batch culture by attaching the 130Z strain to a polymer substance (Urbance et al., *Appl. Microbiol. Biotechnol.*, 65:664, 2004). The present inventors isolated *Mannheimia succiniciproducens* MBEL55E from Korean rumen which has an ability to produce succinic acid with high efficiency (Lee et al., *Appl. Microbiol. Biotechnol.*, 58:663, 2002; KCTC 0769BP, Korean Collection for Type Cultures), and recently announced its whole genome sequences consisting of 2,314,078 base pairs (Hong et al., *Nature Biotechnol.*, 22:1275, 2004).

Especially, the applicants of the present invention created a *Mannheimia* sp. LPK strain (KCTC 10558BP) in which lactate dehydrogenase (ldhA) and pyruvate formate-lyase (pfl) genes are deleted. Also, the present inventors have created a succinic acid overproducing sp. LPK7 strain obtained by deleting phosphotransacetylase (pta) and acetate kinase (ackA) genes from the LPK strain (WO 05/052135 A1). In the succinic acid production process using the above mentioned bacteria, complex media whose components are chemically undefined, which contains peptone, yeast extracts and/or corn steep liquor, have been used.

As stated the above, the compositions of components present in complex media are not consistent and their prices are expensive than those of chemicals used in the preparation of a synthetic medium. Also, use of the complex medium containing the aforementioned components cannot guarantee the production of goods with consistent quality through the culture of microorganisms and unknown components in the complex medium cause an increase in the costs of separation and purification. It has been known that some of these components inhibit cell growth and the production of specific metabolites. Especially, unknown components in a complex medium make it difficult to elucidate cellular metabolic characteristics and restrict the creation of excellent bacteria through metabolic engineering.

Accordingly, it has been reported that synthetic media of *Actinobacillus succinogen* known as an important strain producing succinic acid was developed by employing a single omission technique (McKinlay et al., *Appl. Environ. Microbiol.*, 71:6651, 2005). Since the whole genome information of the bacteria cannot be used, the development of synthetic media was achieved by using the previously known information on synthetic culture media of other bacteria. In other words, a vitamin mixture solution containing 10 kinds of vitamins which was used in the culture of methane producing bacteria was used as vitamin components and an amino acid mixture solution containing 12 kinds of amino acids which was used in the culture of *Haemophilus influenzae* was used as amino acid components. Finally, a synthetic medium containing 3 kinds of amino acids obtained by eliminating each amino acid from the above amino acid mixture solution and the aforementioned 10 kinds of vitamin mixture solution are prepared. However, this method is just one example using the conventional single omission technique. Especially, the culture medium showed cell growth rate of 50% compared with culture media containing 12 kinds of amino acid and 10 kinds of vitamins. Recently, nutrients necessary for the growth of *Lactobacillus plantarum* are identified using a single omission technique and they are used as basic data for the construction of metabolic network using genome information (Teusink et al., *Appl. Environ. Microbiol.*, 71:7253, 2005). However, attempts on the identification of nutrients necessary for the growth of cells or cell lines from genome information of organisms and the development method of a culture medium using thereof are not achieved yet.

Thus, it is desperately in need to develop a method for preparing efficient culture medium of eukaryotic cell or prokaryotic cell, which is more systematical and accurate, and can reduce research costs so that it can substitute for the conventional single omission technique or statistical method requiring many times, many efforts and a huge amount of research costs. For this, the whole metabolic network based on decoded genome information of organism must be first constructed and based on the constructed metabolic network, nutrients certainly necessary for production of target metabolites and growth of eukaryotic or prokaryotic cells are determined to prepare minimal and optimal synthetic media using the nutrients. Particularly, until now, there has been no attempt to develop a culture medium of eukaryotic cell or prokaryotic cells based on the whole metabolic network using the above described genome information.

Also, amino acids such as alanine, asparagine, glutamic acid, histidine, isoleucine and leucine and vitamins such as ascorbic acid are used widely as a major component of a culture medium, however, the effects thereof on the growth of eukaryotic or prokaryotic cells and the production of target metabolites has not been found yet.

Accordingly, in order to efficient culture medium development for eukaryotic or prokaryotic cells, the present inventors have identified nutrients necessary for the production of succinic acid as a target metabolite and cell growth using metabolic network constructed based on the whole genome information of *M. succiniciproducens* MBEL55E, and have developed a minimal and optimal synthetic medium whose components are chemically defined and found the function of the culture medium for synthesizing target metabolites. Based on the above finding, the present invention has been completed.

SUMMARY OF THE INVENTION

It is therefore an object of the present invention to provide a method for developing a minimal synthetic medium, the method comprising constructing a metabolic network using genome information of prokaryotic cell or eukaryotic cell, selecting components of the minimal synthetic medium by removing any one among external metabolites from the constructed metabolic network and conducting metabolic flux analysis using in silico simulation, and determining a final culture medium using by the actual culture.

To achieve the above object, the present invention provides a method for developing a culture medium using in silico analysis and genome information, the method comprising; (a) constructing a metabolic network using genome information of target eukaryotic or prokaryotic cells; (b) removing any one among external metabolites from the constructed metabolic network and conducting metabolic flux analysis using in silico simulation; (c) determining the removed external metabolite as a component of a minimal synthetic medium when a objective function value is 0 after the in silico simulation (herein, the objective function value is 0 if any one of the components required by eukaryotic or prokaryotic cell cannot be produced) or returning to step (b) when the objective function value is not 0; (d) confirming whether a relevant metabolite can be produced internally and used without providing it externally when relevant metabolic reaction formula exists after examining the relevant reaction formula and deficient enzymes through the comparison with other organism species synthesizing the metabolite by itself; (e) determining components of a minimal synthetic medium determined by repeating steps (b)~(d) as a minimal synthetic medium for in silico; and (f) determining a final culture medium after cultivation of target eukaryotic or prokaryotic cells in the determined minimal synthetic medium for in silico. Preferably, the metabolic flux analysis in step (b) is accomplished by constraining the exchange flux or uptake reaction for the metabolite to zero and optimizing for the biomass formation objective reaction.

In one aspect, the present invention provides a method for developing a culture medium for producing succinic acid using in silico analysis and genome information, the method comprising; (a) constructing a metabolic network using genome information of eukaryotic or prokaryotic cells having succinic acid-producing ability; (b) removing any one among external metabolites from the constructed metabolic network and conducting metabolic flux analysis using in silico simulation; (c) determining the removed external metabolite as a component of a minimal synthetic medium when a objective function value is 0 after the in silico simulation (herein, the objective function value is 0 if any one of the components required by eukaryotic or prokaryotic cell(s) cannot be produced) or returning to step (b) when the objective function value is not 0; (d) confirming whether a relevant metabolite can be produced internally and used without providing it externally when relevant metabolic reaction formula exists after examining the relevant reaction formula and deficient enzymes through the comparison with other organism species synthesizing the metabolite by itself; (e) determining components of a minimal synthetic medium determined by repeating steps (b)~(d) as a minimal synthetic medium for in silico; and (f) determining a final culture medium after culturing target eukaryotic or prokaryotic cells having the ability to produce succinic acid in the determined the minimal synthetic medium for in silico. Preferably, the metabolic flux analysis in step (b) is accomplished by constraining the exchange flux or uptake reaction for the metabolite to zero and optimizing for the biomass formation objective reaction.

In another aspect, the present invention provides a culture medium for producing succinic acid, which contains one or more amino acids selected from the group consisting of glucose or other carbon sources, methionine and cysteine, one or more vitamins selected from the group consisting of nicotinic acid, pantothenate, pyridoxine and thiamine, and nucleotide.

In still another aspect, the present invention provides a method for producing succinic acid, the method comprising; culturing bacteria having succinic acid-producing ability using the culture medium for producing succinic acid; and recovering succinic acid from the culture broth.

The above and other objects, features and embodiments of the present invention will be more clearly understood from the following detailed description and the accompanying claims.

DETAILED DESCRIPTION OF THE INVENTION, AND PREFERRED EMBODIMENT THEREOF

Figure 1:
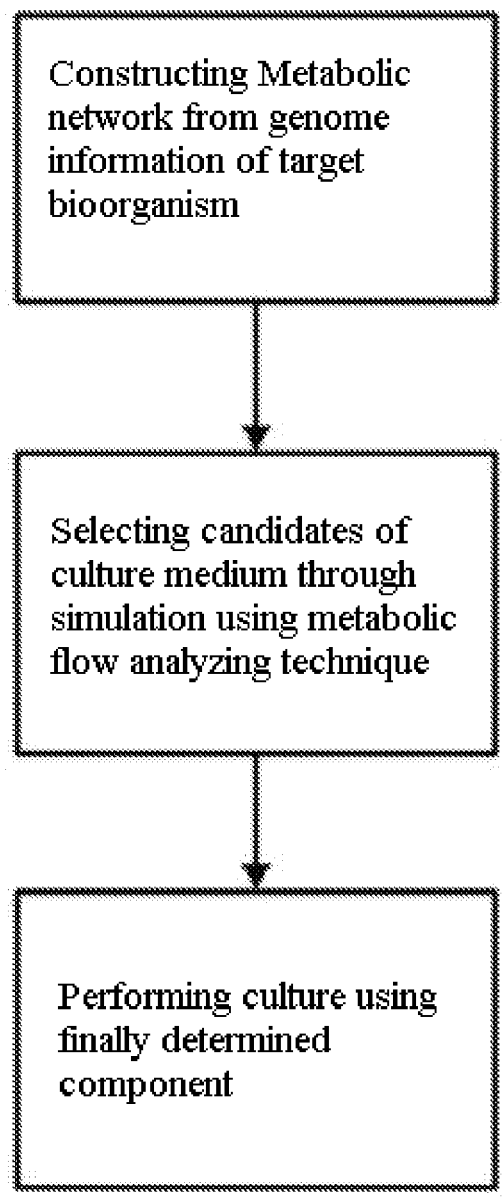
FIG. 1 shows a process of a method for developing a culture medium according to the present invention.

The present invention is relates to the method of a culture medium development and the medium of eukaryotic cell or prokaryotic cell whose whole genome information or some parts of it, enabling the construction of metabolic network thereof is decoded and a method for developing the same.

According to the present invention, the prokaryotic cell or eukaryotic cell is preferably a microorganism having succinic acid-producing ability, but it is not limited thereto, all organism species, whose whole genome information or part thereof is revealed, can preferably be included. All organisms characteristic genome information and whole metabolic network can be constructed using genome information (Forster et al., Genome Research, 13:244, 2003; Ma et al., Bioinformatics, 19:270, 2003; Becker et al., BMC Microbiol., 5:8, 2005). Also, a culture medium can be prepared by identifying nutrients necessary for target metabolite production and growth of eukaryotic or prokaryotic cell using the metabolic network.

Thus, the present invention provides a method for preparing an optimal synthetic medium for the production of a target metabolite and culture of eukaryotic or prokaryotic cell, the method comprises: (a) selecting minimum nutrients necessary for the production of target metabolites and growth of eukaryotic cell or prokaryotic cell based on a metabolic network using whole genome information or part thereof which is enough to construct the metabolic network; (b) preparing a minimal synthetic medium using them; (c) adding components which is not required necessarily, but promotes cell growth. The process of obtaining target metabolites and culturing eukaryotic cell or prokaryotic cell can be conducted using generally known culture method, and methods for separation and purification of metabolites.

In another aspect, the present invention relates to a method for developing a culture medium using in silico analysis and genome information, the method comprising: (a) constructing a metabolic network using genome information of a target eukaryotic cell or prokaryotic cell; (b) removing any one among external metabolites from the constructed metabolic network and conducting metabolic flux analysis using in silico simulation; (c) determining the removed external metabolite as a component of a minimal synthetic medium when a objective function value is 0 after the in silico simulation (herein, the objective function value is 0 if any one of the components required by eukaryotic or prokaryotic cell cannot be produced) or returning to step (b) when the objective function value is not 0; (d) confirming whether a relevant metabolite can be produced internally and used without providing it externally when relevant metabolic reaction formula exists after examining the relevant reaction formula and deficient enzymes through the comparison with other organism species synthesizing the metabolite by itself; (e) determining components of a minimal synthetic medium determined by repeating steps (b)~(d) as a minimal synthetic medium for in silico; and (f) determining a final culture medium after culturing target eukaryotic or prokaryotic cells in the determined the minimal synthetic medium for in silico. Preferably, the metabolic flux analysis in step (b) is accomplished by constraining the exchange flux or uptake reaction for the metabolite to zero and optimizing for the biomass formation objective reaction.

In another aspect, the present invention provides a method for developing a culture medium for producing succinic acid using in silico analysis and genome information, the method comprising; (a) constructing a metabolic network using genome information of eukaryotic cell or prokaryotic cell having succinic acid-producing ability; (b) removing any one among external metabolites from the constructed metabolic network and conducting metabolic flux analysis using in silico simulation; (c) determining the removed external metabolite as a component of a minimal synthetic medium when a objective function value is 0 after the in silico simulation (herein, the objective function value is 0 if any one of the components required by eukaryotic or prokaryotic cell cannot be produced) or returning to step (b) when the objective function value is not 0; (d) confirming whether a relevant metabolite can be produced internally and used without providing it externally when relevant metabolic reaction formula exists after examining the relevant reaction formula and deficient enzymes through the comparison with other organism species synthesizing the metabolite by itself; (e) determining components of a minimal synthetic medium determined by repeating steps (b)~(d) as a minimal synthetic medium for in silico; and (f) determining a final culture medium after culturing target eukaryotic or prokaryotic cells having the ability to produce succinic acid in the determined the minimal synthetic medium for in silico. Preferably, the metabolic flux analysis in step (b) is accomplished by constraining the exchange flux or uptake reaction for the metabolite to zero and optimizing for the biomass formation objective reaction.

In the present invention, the step (f) preferably comprises the substeps of (i) identifying minimum nutrient requirements of the eukaryotic cell or prokaryotic cell by culturing them while adding a specific nutrient one by one to a minimal synthetic medium for in silico and (ii) determining a final culture medium and the inventive method preferably further comprises determining a final culture medium by adding a nutrient which is not necessarily required for growth of eukaryotic cell or prokaryotic cell but promotes growth thereof to the culture medium after the step (f).

In the present invention, in silico simulation in step (b) is preferably conducted under condition containing glucose or other carbon sources.

In the present invention, eukaryotic cell having succinic acid-producing ability is preferably the genus *Mannheimia* and it is preferably *Mannheimia succiniciproducens* MBEL55E (KCTC 0697BP).

In the present invention, the external metabolites in step (b) are preferably one or more selected from the group consisting of amino acids and vitamins and the amino acids are preferably one or more selected from the group consisting of methionine and cysteine, and the vitamins are preferably one or more selected from the group consisting one or more vitamins selected from the group consisting of nicotinic acid, pantothenate, pyridoxine and thiamine.

In the present invention, the nutrients promoting growth are preferably one or more selected from the group consisting of amino acids, vitamins and nucleotides, and the amino acids are preferably one or more selected from the group consisting of alanine, asparagine, glutamic acid, histidine, isoleucine, leucine, phenylalanine, proline, threonine and tryptophane, and the vitamins are preferably one or more selected from the group consisting of ascorbic acid, biotin and folic acid, and the nucleotides are preferably one or more selected from the group consisting of uracil and xanthine.

In another aspect, the present invention relates to a culture medium for producing succinic acid, which contains one or more amino acids selected from the group consisting of glucose or other carbon sources, methionine and cysteine, one or more vitamins selected from the group consisting of nicotinic acid, pantothenate, pyridoxine and thiamine, and nucleotides and a method for producing succinic acid, the method comprising; culturing bacteria having succinic acid producing ability using the above culture medium for producing succinic acid; and recovering succinic acid from the culture broth.

In the present invention, the genus *Mannheimia* alone is shown as an example for a microorganism having succinic acid-producing ability, however, it is obvious to a person skilled in the art that all kinds of prokaryotic cells or eukaryotic cells, whose whole genome information or some parts of the genome information which is enough to construct a metabolic network is decoded, can also be used.

In the present invention, two amino acids and four vitamins which are added to a minimal synthetic medium are major components for growth of eukaryotic cell or prokaryotic cell. Also, ten amino acids, three vitamins and two nucleotides, which are added to a optimal synthetic medium containing the two amino acids and four vitamins, generally have an effect for promoting growth of all kinds of eukaryotic cells or prokaryotic cells and are used widely as major components of a medium, however, the components of the culture medium according to the present invention are not limited to the above various amino acids, vitamins and nucleotides.

EXAMPLES

The present invention will hereinafter be described in further detail by examples. However, it is to be understood that these examples can be modified into other various forms, and the scope of the present invention is not intended to be limited to such examples.

Example 1

Construction of *Mannheimia* Metabolic Network and In Silico Analysis (1) Construction of Metabolic Network In the present invention, a novel metabolic network is constructed to develop a synthetic medium of *Mannheimia*. Specifically, a relevant metabolic pathway is constructed after gene regions are assumed based on the whole genome information of *Mannheimia* and the function of each gene is determined, and cell metabolism is probed in real-time therefrom.

(2) Metabolic Flux Analysis Using In Silico Simulation

To predict components of a synthetic medium for growth of *Mannheimia* and the production of succinic acid, metabolic flux analysis method was used based on the constructed whole metabolic network of *Mannheimia*.

If all metabolites, metabolic pathways and the stoichiometric matrix in the pathways ($S_{ij}^T$, metabolite i in the j reaction) are known, the metabolic flux vector ($v_j$, flux of j pathway) can be calculated, in which a change in the metabolite X with time can be expressed as the sum of all metabolic fluxes. Assuming that a change in X with time is constant i.e., under the assumption of the quasi-steady state, the following equation is defined.

$$S^T v = dX/dt = 0$$

Wherein, $S^T v$ is a change in the metabolite with time, X is concentration of metabolites and t is time The optimal metabolic flux distribution is then calculated by a linear programming using specific objective functions and various physicochemical equations where the flux value of a specific metabolic reaction can be limited to a specific range. This can be calculated as follows:

minimize/maximize: $Z = \Sigma\ c_i v_i$ s.t. $S^T v = 0$ and $\alpha_{min,i} \leq v_i \leq \alpha_{max,i}$ wherein $c_i$ is weighted value, and $v_i$ is metabolic flow. Generally, the maximization of biomass formation rate (i.e., specific growth rate), the maximization of metabolite production and the minimization of byproduct production, and the like, are used as the objective functions. $\alpha_{max,i}$ and $\alpha_{min,i}$ are limit values which each metabolic flux can have, and they can assign the maximum and minimum values permissible in each metabolic flux. Particularly, it has been reported that the case of the maximization of biomass formation is most similar to physiological phenomena which actual cell shows (Ibarra, R. U., Edwards, J. S., and Palsson, B. Ø ., 2002).

A minimal synthetic medium is determined using the metabolic flux analysis method in Example 2. The analysis of metabolic flux is performed using a MetaFluxNEt program (Lee et al., Bioinformatics, 19:2144, 2003).

Example 2

Determining Components of Minimal Synthetic Medium Using In Silico Analysis

Whether there is a problem in biomass formation, was examined by conducting metabolic flux analysis under the condition of eliminating uptake of a possible external metabolite one by one from the whole metabolic network of *Mannheimia*. Herein, glucose was basically contained as a carbon source and uptake rate of a relevant metabolite was set to 0 uptake of external metabolites. Also, biomass formation was used as the objective function for analyzing metabolic flow. When a complex medium is predicted in other carbon source, metabolic flux analysis was performed in condition where the relevant carbon source is basically contained.

In the case of where the objective function value is 0 as a result of analyzing metabolic flow since any one of the components, which is required by a strain, is not produced when a relevant metabolite is eliminated, the relevant metabolite is determined as a candidate of a minimal synthetic medium predicted from the metabolic network of *Mannheimia*. This is to examine whether candidate components can be synthesized and thus cell growth is possible or not. Accordingly, if it is confirmed through metabolic flux analysis that a relevant metabolite is produced, it was determined that the metabolite does not need to be provided by means of an external medium. On the contrary, if it is confirmed through metabolic flux analysis that biomass is not produced when a specific component is deficient, it was determined that the specific component must be provided through an external medium.

Also, in order to find out the reason why a relevant metabolite cannot be produced, relevant metabolic reaction formula and deficient enzymes were examined through the comparison with other organism species synthesizing the metabolite by itself and analysis. If the relevant metabolic reaction equation exists, whether the relevant metabolite can be produced internally and used without providing the metabolite externally was examined, thus determining a final minimal synthetic medium for in silico.

Then, actual culture was performed based on the minimal synthetic medium for in silico. Actual cell needs all components including vitamins, amino acids, nucleotides etc. According to the kind of cells, it synthesizes the components by itself, or the components are provided externally in a case of it does not having the ability to synthesize. In experiment, although a relevant metabolic network of a specific component exists, relevant synthesis genes are not expressed sufficiently enough for regulatory mechanism in cells, and thus, the specific component must be provided through an external medium to promote cell growth. For this reason, minimal nutrient requirements of a relevant strain were confirmed through final actual culture experiment while adding a specific nutrient one by one to a minimal synthetic medium for in silico.

Also, after determining the minimal synthetic medium, an optimal synthetic medium was determined by identifying components that are not required necessarily for the growth of a strain but promotes growth of a strain based on the minimal synthetic medium. For this, the results obtained by adding specific nutrients one by one to the above described minimal synthetic medium for in silico. The above described method for searching candidate components for a synthetic medium using metabolic flow has an advantage in that even the effect of a deficiency in metabolic network which is not shown can be considered, unlike methods for simply searching whether relevant metabolic network of candidate components exists.

(1) Amino Acid

In case of metabolic network of *Mannheimia*, partial synthetic pathway of components of amino acids shown in table 1 is deleted, metabolic flow for synthesizing the relevant metabolites is impossible. Thus, the components shown in Table 1 must be added to a minimal synthetic medium.

TABLE 1

Relevance of amino acids predicted based on metabolic network

| Amino acid | Synthesis through metabolic flux | Synthesis through metabolic flux |
|---|---|---|
| Methionine | Methionine metabolism | NO |
| Cysteine | Cysteine metabolism | NO |

Although amino acid synthesis metabolic network exists, relevant genes are not expressed sufficiently enough for regulating mechanism in cells and thus promotion of cell growth can be achieved by uptake from an external medium. So, identification of nutrient requirements of relevant amino acids for optimal cell growth using actual experiment is necessary.

Figure 2:
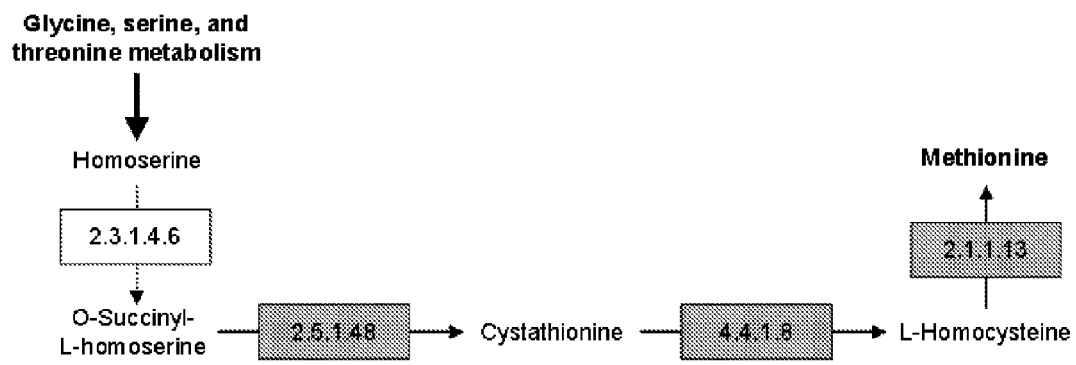
FIG. 2 shows metabolic networks for synthesizing deficient amino acid (A: methionine; B: cysteine). Rectangular filled with grey represents the gene present in the metabolic network of *M. succiniciproducens*. On the other hand, rectangular filled with white indicates the gene absent in the metabolic network of *M. succiniciproducens*.
Figure 2:
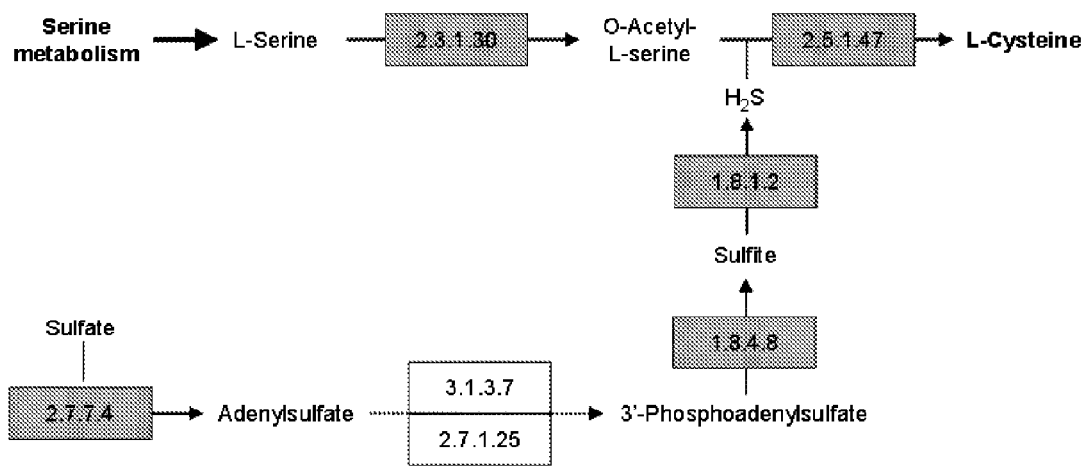
Figure 3:
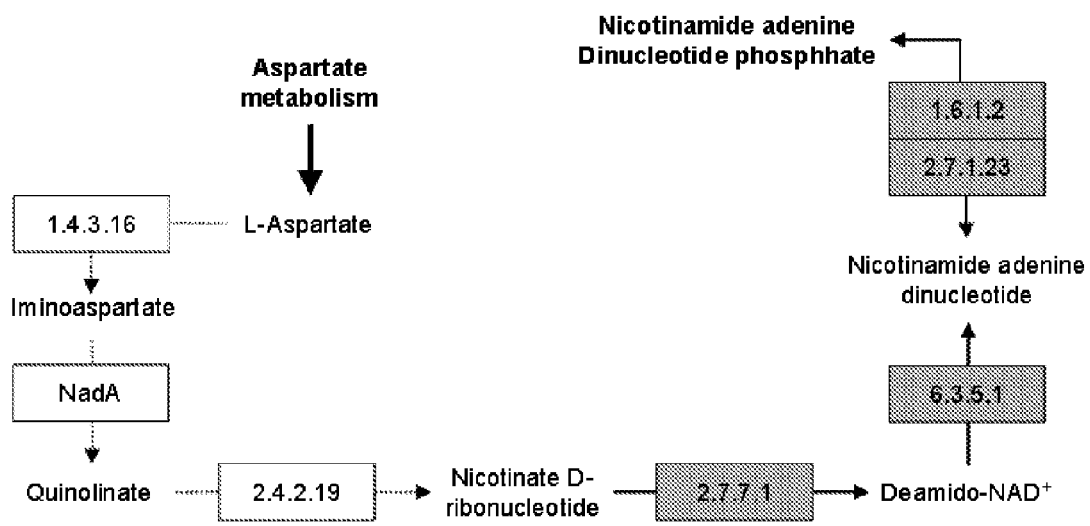
FIG. 3 shows metabolic networks for synthesizing deficient vitamin (A: nicotinic acid; B: pantothenate; C: pyridoxine; and D: thiamine). Rectangular filled with grey represents the gene present in the metabolic network of *M. succiniciproducens*. On the other hand, rectangular filled with white indicates the gene absent in the metabolic network of *M. succiniciproducens*.
Figure 3:
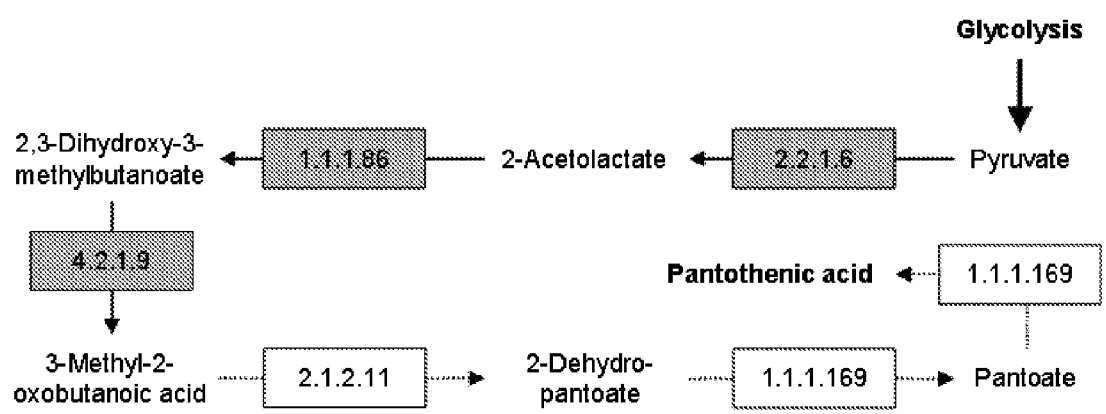
Figure 3:
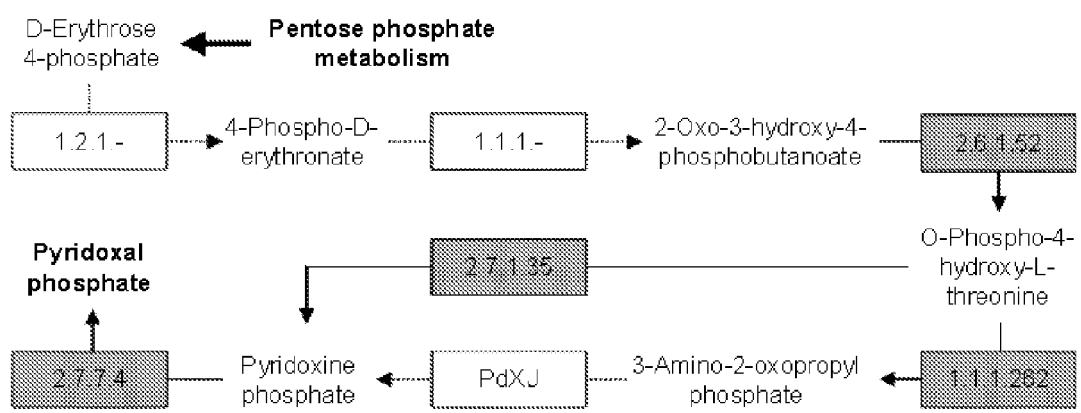
Figure 3:
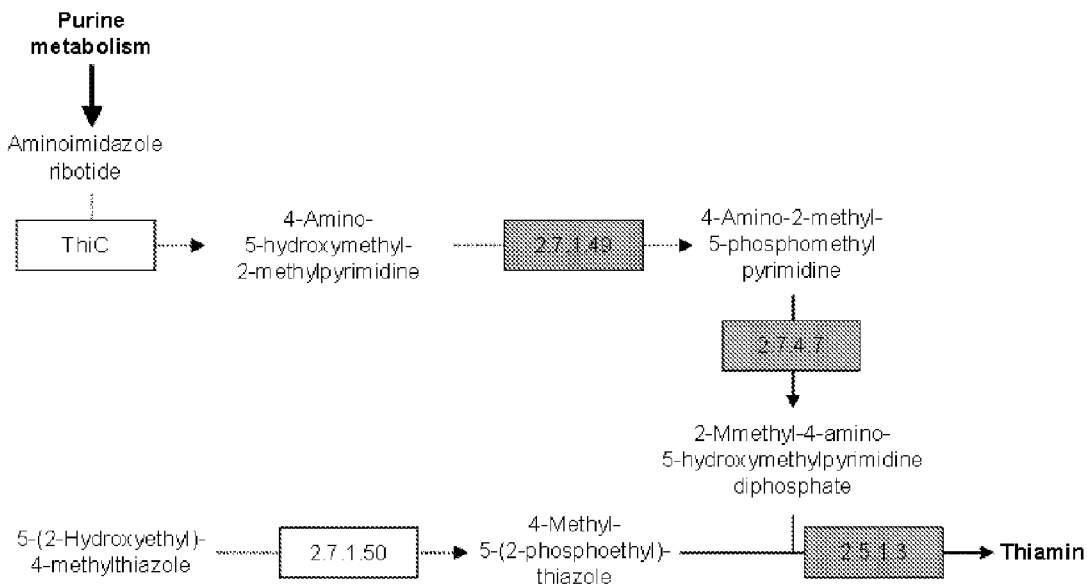

As a result of the examination of metabolic equation and deficient enzymes from a metabolic network of *Mannheimia*, as shown in FIGS. 2(A) and 2(B), in case of methionie, homoserine O-succinyltransferase (E. C. 2.3.1.46) was deleted and in case of cysteine, 3'(2'),5'-bisphosphate nucleotidase/adenylyl-sulfate kinase (E. C. 3.1.3.7/E. C. 2.7.1.25) were deleted.

(2) Vitamin

In case of vitamins, since biosynthetic pathway of nicotinic acid, pantothenate, pyridoxine and thiamine does not exist, it was confirmed that they are not synthesized by metabolic flow. Thus, the components shown in Table 2 were certainly added to a synthetic medium.

TABLE 2

Relevance of vitamins predicted based on metabolic network

| Vitamin | Function | Synthesis through metabolic flow |
|---|---|---|
| Nicotinic acid | Nicotinic acid metabloism | NO |
| Pantothenate | Pantothenate and CoA biosynthesis | NO |
| Pyridoxine | Pyridoxine metabolism | NO |
| Thiamine | Thiamine metabolism | NO |

As a result of the examination of metabolic reaction equation and deficient enzymes in the metabolic network of *Mannheimia*, it was confirmed that as shown in FIG. 3(A)~(D), by deficient enzymes, relevant metabolites shown in Table 2 need to be provided externally.

(3) Nucleotide

In case of nucleotides, it is confirmed that all biosynthetic pathways exist and there are no components which need to be provided through an external medium for cell growth. However, although nucleotide synthesis metabolic network exists, relevant genes are not expressed sufficiently enough for regulating mechanism in cells and thus, promotion of cell growth can be achieved by uptake from an external medium. So, identification of nutrient requirements of relevant nucleotides for optimal cell growth using actual experiment is necessary.

Example 3

Preparation of Culture Medium According to the Present Invention (1) Composition of Liquid Culture Medium Necessary components were predicted using information on cell growth and nutrients obtained based on the whole metabolic network using genome information in Examples 1 and 2. Also, nutrients required for the growth of *Mannheimia* and the production of succinic acid were identified through actual experiment. Based on this, minimal and optimal synthetic media were developed. Table 3, 4, 5 and 6 are the compositions of components of a limited culture medium, a complex medium, a minimal synthetic medium and an optimal medium for culture of *Mannheimia succiniciproducens* MBEL55E, respectively.

TABLE 3

Composition of limited medium

| component | concentration |
|---|---|
| NaCl | 1 g/L |
| $K_2HPO_4$ | 8.709 g/L (50 mM) |
| Glucose | 18.02 g/L (100 mM) |
| $CaCl_2 \cdot 2H_2O$ | 0.02 g/L |
| $MgCl_2 \cdot 6H_2O$ | 0.2 g/L |
| Trace element solution | 1.0 ml/L |

TABLE 4 composition of complex medium (Limited medium of Table 3 + Yeast extract)

| component | concentration |
|---|---|
| Yeast extract | 5 g/L |

A minimal synthetic medium was prepared by adding two amino acids and four vitamins selected primarily, which cannot be produced by cell itself using the constructed metabolic network to a limited medium. Also, the preparation of the medium was completed by confirming that cell growth and the production of succinic acid was not achieved, if the two amino acids and four vitamins were eliminated from the minimal synthetic medium.

An optimal synthetic medium was prepared by adding eighteen amino acids, ten vitamins and six nucleotides one by one to the minimal synthetic medium to culture cells and secondarily selecting fifteen components having enhanced succinic acid production and cell growth compared to those obtained in the minimal synthetic medium.

A limited medium, a complex medium, a minimal synthetic medium and an optimal synthetic medium were prepared as follows: nutrients of the limited medium and the complex culture medium, which have the compositions and concentrations shown in Table 3 and Table 4 were dissolved in deionized distilled water, respectively. pH of the culture medium was adjusted to 7 using 5N NaOH solution. The prepared culture medium was put into glass Erlenmeyer flask and $CO_2$ gas was injected into the flask for ten minutes and then, the culture medium was gas-tightly sealed with a cork. The limited medium and the complex medium into which $CO_2$ gas was injected were pressurized and sterilized (121° C., 15 min), and they were cooled to room temperature and then used as culture media. The yeast extract added to the complex medium was Bacto™ Yeast Extract manufactured and sold by BacBecton, Dickinson and Company (Sparks, Md., USA).

TABLE 5

Composition of minimal synthetic medium (limited medium + two amino acids + four vitamins)

| | component | concentration (g/L) |
|---|---|---|
| 2 amino acids | Methionine | 0.5 |
| | Cysteine | 0.5 |
| 4 vitamins | Nicotinic acid | 0.005 |
| | Ca-Pantothenate | 0.005 |
| | Pyridoxine•HCl | 0.005 |
| | Thiamine•HCl | 0.005 |

TABLE 6

Composition of optimal synthetic medium (minimal synthetic medium + ten amino acids + three vitamins + two nucleotides)

| | component | concentration (g/L) |
|---|---|---|
| 10 amino acids | Alanine | 0.5 |
| | Asparagine | 0.5 |
| | Glutamic acid | 0.5 |
| | Histidine | 0.5 |
| | Isoleucine | 0.5 |
| | Leucine | 0.5 |
| | Phenylalanine | 0.5 |
| | Proline | 0.5 |
| | Threonine | 0.5 |
| | Tryptophane | 0.5 |
| 3 vitamins | Ascorbic acid | 0.005 |
| | Biotin | 0.005 |
| | Folic acid | 0.005 |
| 2 nucleotides | Uracil | 0.01 |
| | Xanthine | 0.01 |

A minimal synthetic medium and an optimal synthetic medium were prepared by adding a mixture solution of amino acids, vitamins and nucleotides, which has compositions and concentrations shown in Table 5 and Table 6 to limited medium. pH of the culture medium was adjusted to 7 using 5N NaOH solution. The mixture solution used in the preparation of the complex medium was prepared by mixing each 1 ml of each concentrated amino acids solution, each 0.5 ml of each concentrated vitamin solution, each 0.5 ml of each concentrated nucleotide solution. The mixture solution was used after sterilization by passing the solutions through a membrane having pore size of 0.2 μm.

Example 4

Culture of *Mannheimia succiniproducens* MBEL55E and Analysis of Succinic acid Concentration (1) Culture of *Mannheimia succiniproducens* MBEL55E The bacteria were cultivated in a test tub, a flask, and a fermentor. Test tube culture was performed as follows: 20 ml of the culture medium was transferred to 80 ml of test tube and then, 1 ml of *Mannheimia succiniciproducens* MBEL55E kept under −70° C. was inoculated into the test tube. In case of *Mannheimia succiniciproducens* MBEL55E kept in temperature below −70° C., the culture was performed in a complex medium. Accordingly, since yeast extracts used in the complex medium remained, washing was performed at the time of primary inoculation to remove them from *Mannheimia succiniciproducens* MBEL55E. Specifically, the inoculated solution was centrifuged at 5000 rpm, 4° C., for 5 min and the supernatant was removed and then washed using relevant medium. The washing was repeated three times. The culture was performed up to optical density (OD600) of 1.5 in a 39° C. incubator after CO2 gas was injected into the inoculated test tube. To enhance an adaptation applicable ability of cells to a new relevant culture medium and promote activities thereof, subculture was repeated ten times. After the culture broth was mixed with 30% (w/v) glycerol solution in a ratio of 1:1 (v/v) and kept below −70° C., it was used as inoculum in a further experiment.

The flask culture was performed by inoculating 2.5 ml of the culture broth prepared by culturing the inoculated bacteria up to 1.0 of optical density (OD600) in the test tube to 500 ml flask containing 250 ml of culture medium. The flask culture was performed in the same condition as that of the test tube culture.

The fermentor culture was performed using 6.6 liter Bioflo 3000 fermentor (New Brunswick Scientific Co., Ediso, N.J.) containing 2.5 liter of culture medium. 250 ml of flask culture broth was used as inoculated bacteria, pH of culture broth in a fermentor was adjusted to 6.5 using ammonia solution. A continuous supply of 1.25 l/min of CO2 maintains anaerobic condition in the fermentor and provides CO2 necessary for cell growth and the production of succinic acid. Setting impeller to rotate at 250 rpm in the fermentor induced complete mixing of culture broth.

(2) Analysis of Succinic Acid Concentration According to *Mannheimia succiniproducens* MBEL55E Each 20 ml of culture was taken from the fermentor and used in analysis. Growth of *Mannheimia succiniciproducens* MBEL55E was measured by measuring optical density using spectrophotometer (Pharmacia Biotec, Cambridge, England). Measurement of optical density was performed at 600 nm wavelength of spectrophotometer.

The concentrations of consumed glucose, produced succinic acid and various organic acid were analyzed using HPLC (High performance liquid chromatography; Hitachi Co., Tokyo, Japan with an Aminex HPX-87H column).

Samples used in analysis were obtained by passing the supernatant through a membrane having pore size of 0.2 μm after centrifugation at 12000 rpm, for 6 min.

Example 5

Effect of Synthetic Medium According to the Present Invention

Figure 4:
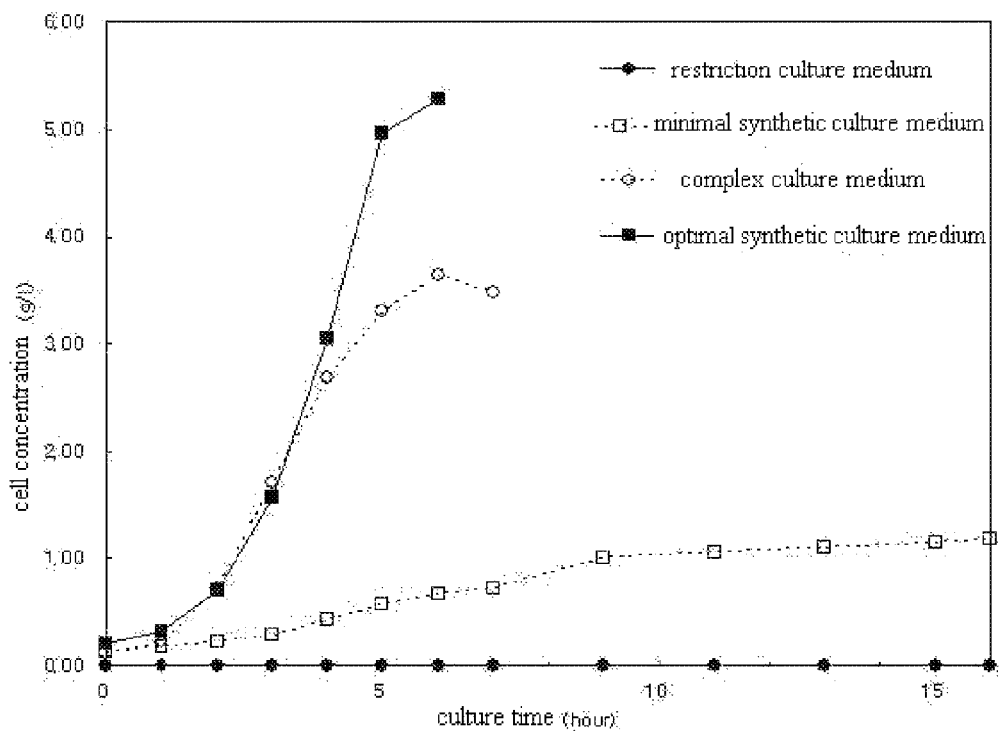
FIG. 4 is a graph showing the growth of *Mannheimia* cultured in a culture medium according to the present invention.
Figure 5:
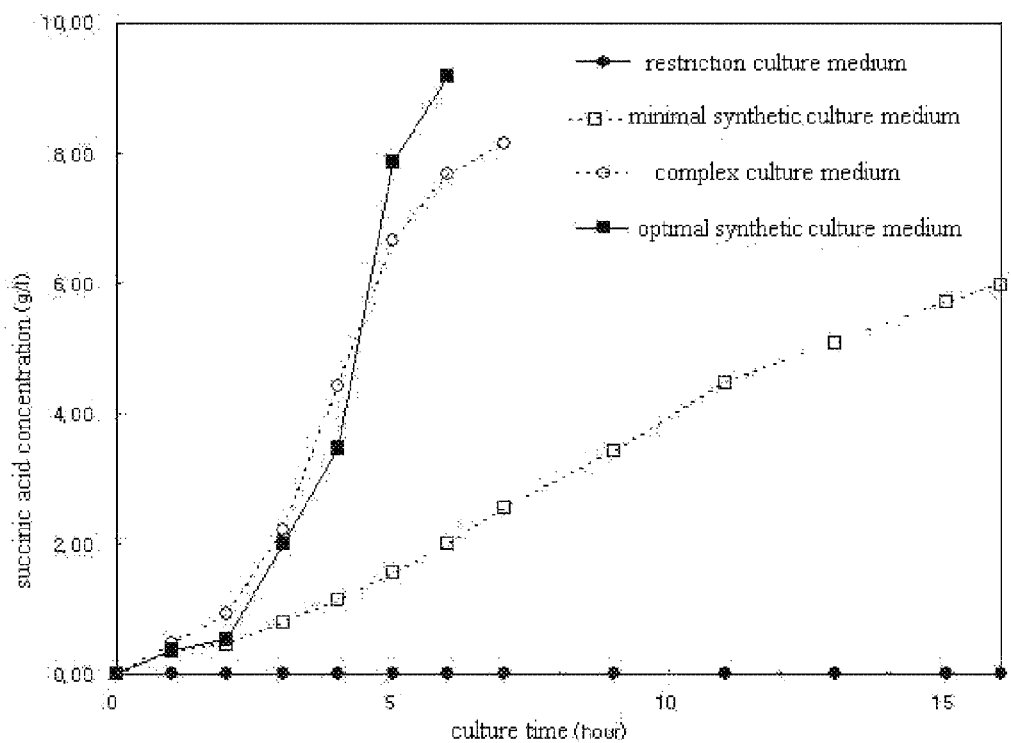
FIG. 5 is a graph showing the production of succinic acid of *Mannheimia* cultured in a culture medium according to the present invention.

To confirm the effect of the prepared synthetic medium, *Mannheimia succiniciproducens* MBEL55E was cultured in the complex medium, the limited medium, the minimal synthetic medium and the optimal synthetic medium as shown in Example 4, respectively. As shown in FIGS. 4 and 5, in case of the limited culture medium, cell growth and succinic acid production were not observed.

However, in case when *Mannheimia succiniciproducens* MBEL55E was cultivated in the inventive minimal and optimal synthetic media, the cell growth was confirmed. Particularly, in case of *Mannheimia succiniciproducens* MBEL55E was cultured in the optimal synthetic medium, a final cell concentration was 51% higher than that cultured in the generally used, complex medium and a final succinic acid concentration was also 13% higher than that cultured in the generally used, complex medium. Especially, succinic acid productivity in the optimal synthetic medium was 55% higher than that in the complex medium, suggesting that use of the optimal synthetic medium promotes cell growth and succinic acid production.

TABLE 7 concentrations of cells and succinic acid in each culture medium

| Culture media | Max. specific growth rate $(h^{-1})$ | Final cell conc. (g/L) | Final succinic acid conc. (g/L) | Productivity of succinic acid (g/L/h) |
|---|---|---|---|---|
| limited medium | 0 | 0 | 0 | 0 |
| Complex medium | 1.03 | 3.482 | 8.104 | 1.21 |
| Optimal synthetic medium | 0.80 | 5.280 | 9.185 | 1.88 |
| Minimal synthetic medium | 0.28 | 1.183 | 5.943 | 0.44 |

The effect of the inventive minimal and optimal synthetic media is further supported by the result shown in Table 7.

As described above, the present invention is effective in developing a culture medium of prokaryotic cell or eukaryotic cell whose whole genome information or some parts of genome information, which is enough to construct a metabolic network, is decoded using in silico analysis. According to the present invention, the present invention is more accurate and systematic compared with conventional methods and can reduce time, effort and costs for manufacturing. Also, it can be effectively used in developing culture media of various microorganisms for producing target metabolites using a metabolic network prepared based on genome information.

While the present invention has been described with reference to the particular illustrative embodiment, it is not to be restricted by the embodiment but only by the appended claims. It is to be appreciated that those skilled in the art can change or modify the embodiment without departing from the scope and spirit of the present invention.

What is claimed is:

1. A method for developing a culture medium using in silico analysis and genome information, comprising the steps of:
    (a) constructing a metabolic network using genome information of target eukaryotic cell or prokaryotic cell;
    (b) removing any one among external metabolites from the constructed metabolic network and conducting metabolic flux analysis using in silico simulation;
    (c) determining the removed external metabolite as a component of a minimal synthetic medium when a objective function value is 0 after the in silico simulation, wherein the objective function value is 0 if any one of the components required by eukaryotic or prokaryotic cell cannot be produced, or returning to step (b) when the objective function value is not 0;
    (d) confirming whether a relevant metabolite can be produced internally and used without providing it externally when relevant metabolic reaction formula exists after examining the relevant reaction formula and deficient enzymes through comparison with other organism species synthesizing the metabolite by itself;
    (e) determining components of a minimal synthetic medium determined by repeating steps (b) to (d) as a minimal synthetic medium for in silico; and
    (f) determining a final culture medium after culturing target eukaryotic or prokaryotic cells in the determined minimal synthetic medium for in silico.

2. The method according to claim 1, wherein the step (f) comprises the substeps of (i) identifying minimum nutrient requirements of the eukaryotic cell or prokaryotic cell by culturing them while adding a specific nutrient one by one to a minimal synthetic medium for in silico and (ii) determining a final culture medium.

3. The method according to claim 1, wherein the step (f) further comprises determining a final culture medium by adding a nutrient which is not necessarily required for growth of eukaryotic cell or prokaryotic cell but promotes growth thereof to the culture medium after the step (f).

4. The method according to claim 1, wherein said in silico simulation in step (b) is conducted in a condition including glucose or other carbon sources.

5. A method for developing a culture medium for producing succinic acid using in silico analysis and genome information, comprising the steps of:
    (a) constructing a metabolic network using genome information of eukaryotic cell or prokaryotic cell having succinic acid-producing ability;
    (b) removing any one among external metabolites from the constructed metabolic network and conducting metabolic flux analysis using in silico simulation;
    (c) determining the removed external metabolite as a component of a minimal synthetic medium when a objective function value is 0 after the in silico simulation, wherein the objective function value is 0 if any one of the components required by eukaryotic or prokaryotic cell cannot be produced, or returning to step (b) when the objective function value is not 0;
    (d) confirming whether a relevant metabolite can be produced internally and used without providing it externally when relevant metabolic reaction formula exists after examining the relevant reaction formula and deficient enzymes through the comparison with other organism species synthesizing the metabolite by itself;
    (e) determining components of a minimal synthetic medium determined by repeating steps (b) to (d) as a minimal synthetic medium for in silico; and
    (f) determining a final culture medium after culturing target eukaryotic or prokaryotic cells having the ability to produce succinic acid in the determined the minimal synthetic medium for in silico.

6. The method according to claim 5, wherein the step (f) comprises the substeps of (i) identifying minimum nutrient requirements of the eukaryotic cell or prokaryotic cell by culturing them while adding a specific nutrient one by one to a minimal synthetic medium for in silico and (ii) determining a final culture medium.

7. The method according to claim 5, wherein the step (f) further comprises determining a final culture medium by adding a nutrient which is not necessarily required for growth of eukaryotic cell or prokaryotic cell but promotes growth thereof to the culture medium after the step (f).

8. The method according to claim 5, wherein said in silico simulation in step (b) is conducted under conditions containing glucose or other carbon sources.

9. The method according to claim 5, wherein said prokaryotic cell having succinic acid-producing ability is the genus *Mannheimia*.

10. The method according to claim 9, wherein said genus *Mannheimia* is *Mannheimia succiniciproducens* MBEL55E (KCTC0697BP).

11. The method according to claim 5, wherein said external metabolites is one or more selected from group consisting of amino acids and vitamins.

12. The method according to claim 11, wherein said amino acid is selected from group consisting of methionine and cysteine.

13. The method according to claim 11, wherein said vitamin is one or more selected from group consisting of nicotinic acid, pantothenate, pyridoxine and thiamine.

14. The method according to claim 7, wherein component promoting growth is one or more selected from group consisting of amino acids, vitamins and nucleotides.

15. The method according to claim 14, wherein said amino acid is one or more selected from group consisting of alanine, asparagine, glutamic acid, histidine, isoleucine, leucine, phenylalanine, proline, threonine and tryptophane.

16. The method according to claim 14, wherein said vitamin is one or more selected from group consisting of ascorbic acid, biotin and folic acid.

17. The method according to claim 16, wherein said nucleotide is one or more selected from group consisting of uracil and xanthine.

* * * * *